US011457868B2

(12) United States Patent
Brook et al.

(10) Patent No.: US 11,457,868 B2
(45) Date of Patent: Oct. 4, 2022

(54) CONDUCTIVE TRANSFER

(71) Applicant: CONDUCTIVE TRANSFERS LIMITED, Barnsley (GB)

(72) Inventors: Paul Timothy Brook, Barnsley (GB); Mark John Catchpole, Ely (GB); Steven Paul Sutcliffe, Doncaster (GB)

(73) Assignee: CONDUCTIVE TRANSFERS LIMITED, Barnsley (GB)

( * ) Notice: Subject to any disclaimer, the term of this patent is extended or adjusted under 35 U.S.C. 154(b) by 0 days.

(21) Appl. No.: 17/609,907

(22) PCT Filed: May 5, 2020

(86) PCT No.: PCT/GB2020/000046
§ 371 (c)(1),
(2) Date: Nov. 9, 2021

(87) PCT Pub. No.: WO2020/225519
PCT Pub. Date: Nov. 12, 2020

(65) Prior Publication Data
US 2022/0202363 A1 Jun. 30, 2022

(30) Foreign Application Priority Data
May 9, 2019 (GB) ...................................... 1906548

(51) Int. Cl.
*A61B 5/00* (2006.01)
*A61N 1/04* (2006.01)
(Continued)

(52) U.S. Cl.
CPC .......... *A61B 5/6804* (2013.01); *A61N 1/0452* (2013.01); *A61N 1/0484* (2013.01);
(Continued)

(58) Field of Classification Search
CPC .. A61N 1/0452; A61N 1/0472; A61N 1/0476; A61N 1/0484; A61B 5/25;
(Continued)

(56) References Cited

U.S. PATENT DOCUMENTS 7,592,276 B2 * 9/2009 Hill .................... D03D 15/46
313/511
10,328,677 B2 * 6/2019 Schwarz .................. B32B 5/02
(Continued)

FOREIGN PATENT DOCUMENTS

GB       2555592 A      5/2018

OTHER PUBLICATIONS

Corresponding International Patent Application No. PCT/GB2020/000046, International Search Report and Written Opinion, dated Jul. 29, 2020.
(Continued)

*Primary Examiner* — Eugene T Wu
(74) *Attorney, Agent, or Firm* — Cooper Legal Group, LLC

(57) ABSTRACT

A conductive transfer for application to an article comprises first and second non-conductive layers and a conductive layer positioned between the two non-conductive layers. The conductive transfer further comprises an adhesive layer for adhering the conductive transfer to an article, such as a wearable item. The conductive layer comprises a plurality of tessellated cells defined by a printed conductive ink. The conductive layer comprises a main element and an input track with the plurality of tessellated cells being comprised over the input track of said conductive layer.

22 Claims, 13 Drawing Sheets

(51) Int. Cl.
   *B41M 3/12* (2006.01)
   *H05K 3/00* (2006.01)
   *H05K 3/20* (2006.01)

(52) U.S. Cl.
   CPC ............. *B41M 3/12* (2013.01); *H05K 3/0058* (2013.01); *H05K 3/207* (2013.01)

(58) Field of Classification Search
   CPC .. A61B 5/256; A61B 5/27; A61B 5/28; A61B 5/6802; A61B 5/6804; A61B 5/6805; A61B 5/6806
   See application file for complete search history.

(56) References Cited

U.S. PATENT DOCUMENTS

| | | | |
|---|---|---|---|
| 2004/0051082 A1* | 3/2004 | Child | D06M 15/248 252/500 |
| 2008/0083721 A1* | 4/2008 | Kaiserman | H05B 3/342 219/211 |
| 2019/0053372 A1 | 2/2019 | Kwon et al. | |

OTHER PUBLICATIONS

Corresponding International Patent Application No. PCT/GB2020/000046, International Preliminary Report on Patentability, dated Mar. 30, 2021.

* cited by examiner

CONDUCTIVE TRANSFER

CROSS REFERENCE TO RELATED APPLICATIONS

This application claims priority from United Kingdom Patent Application number GB 19 06 548.1, filed on 9 May 2019, the whole contents of which are incorporated herein by reference.

BACKGROUND OF THE INVENTION

The present invention relates to a conductive transfer, an article comprising a conductive transfer and a method of producing a conductive transfer.

Conductive transfers such as that disclosed by the applicant in patent GB 2 555 592 provide a means by which thin, lightweight and washable conductive elements can be incorporated into flexible items, for example, wearable items such as items of clothing. Such transfers may provide an electrical circuit to an electronic device utilized as part of the clothing. In some applications, the conductive transfer covers a large area of the clothing requiring large amounts of conductive ink to be used.

Furthermore, repeated washing and standard wear-and-tear can cause a transfer to suffer from damage or degradation resulting in a loss of functionality in respect of the transfer's electrical performance. In addition, conventional manufacturing processes for textiles can also lead to damage to the transfer before the item of clothing has left the manufacturing facility. In particular, care must be taken not to stitch over the conductive transfer and this can limit the locations of transfers placed in items of clothing.

US 2008/083721 (Kaiserman, Terrance et al) describes a heated textile comprising a conductive layer disposed between two dielectric layers. The conductive layer comprises a conductive ink composition and defines a circuit. The disclosure indicates that the ink used to form the conductive layer should be chosen to provide flexibility and durability of the conductive layer.

There therefore remains a need to improve existing transfers to enable them to be utilized more flexibly and in more complex applications.

BRIEF SUMMARY OF THE INVENTION

According to an aspect of the present invention, there is provided a conductive transfer for application to an article, as claimed in claim 1.

According to a further aspect of the present invention there is provided a method of producing a conductive transfer for application to an article, as claimed in claim 19.

Embodiments of the invention will be described, by way of example only, with reference to the accompanying drawings. The detailed embodiments show the best mode known to the inventor and provide support for the invention as claimed. However, they are only exemplary and should not be used to interpret or limit the scope of the claims. Their purpose is to provide a teaching to those skilled in the art. Components and processes distinguished by ordinal phrases such as "first" and "second" do not necessarily define an order or ranking of any sort.

DETAILED DESCRIPTION OF EMBODIMENTS OF THE INVENTION

FIG. 1

Figure 1:
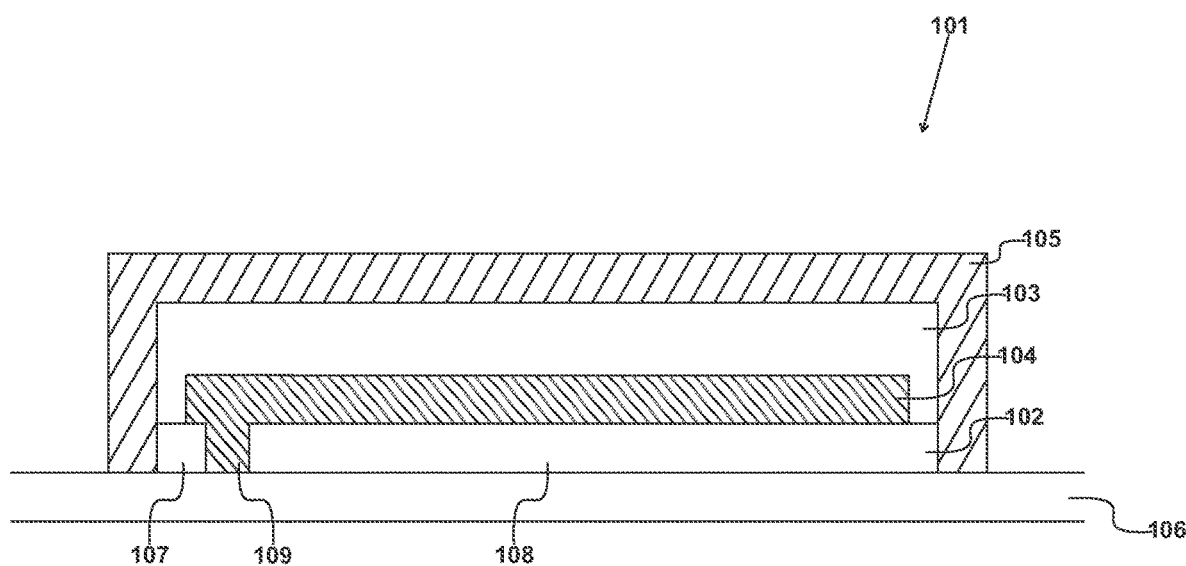
FIG. 1 shows a conductive transfer for application to an article.

A conductive transfer in accordance with the present invention aims to provide a suitable transfer which can be utilized in a wide variety of applications utilizing conventional manufacturing techniques and which can withstand conventional washing techniques and standard use.

An example of such a conductive transfer which is suitable for application to an article, is represented in cross sectional schematic view as conductive transfer 101. It is appreciated that, in this schematic view, conductive transfer 101 is shown having increased thickness. In practice, conductive transfer 101 is typically in the region of between half a millimeter (0.5 mm) and five millimeters (5 mm) in thickness.

Conductive transfer 101 comprises a first non-conductive layer 102 and a second non-conductive layer 103. Conductive transfer 101 further comprises a conductive layer 104, which is positioned between first non-conductive layer 102 and second non-conductive layer 103. Conductive transfer 101 also comprises an adhesive layer 105 which is suitable for adhering the conductive transfer to an article, such as the wearable item depicted in FIG. 8.

In the embodiment, each of the layers are printed onto a transfer substrate 106 which can be removed following an application of heat and/or pressure in line with the method of producing the conductive transfer as will be described with respect to FIG. 5. In this example, first non-conductive layer 102 is printed onto transfer substrate 106, with the following layers being printed thereon in sequence of conductive layer 104, non-conductive layer 103 and adhesive layer 105.

In the embodiment, non-conductive layer 102 is printed in an arrangement which produces areas of non-conductive ink and areas without non-conductive ink. In this cross-sectional view, portions 107 and 108 of non-conductive layer 102 provide areas of non-conductive ink and portion 109 presents an area in non-conductive layer 102 which does not comprise non-conductive ink. Consequently, when conductive layer 104 is printed, conductive ink covers portion 109 to provide a section of conductive ink which can be used as an electrical contact point as part of an electrical circuit.

In the embodiment, non-conductive layers 102 and 103 comprise any suitable printing ink for encapsulating the conductive layer 104. A suitable printing ink may include a water-based printing ink; an ultraviolet cured printing ink; a solvent based ink; or a latex printing ink. It is appreciated that, in alternative embodiments, other suitable non-conductive encapsulating inks may be utilized.

In the embodiment, conductive layer 104 comprises any suitable conductive printing ink, for example, a conductive ink comprising silver. Other conductive inks such as those including copper may also be utilized.

FIG. 2

Figure 2:
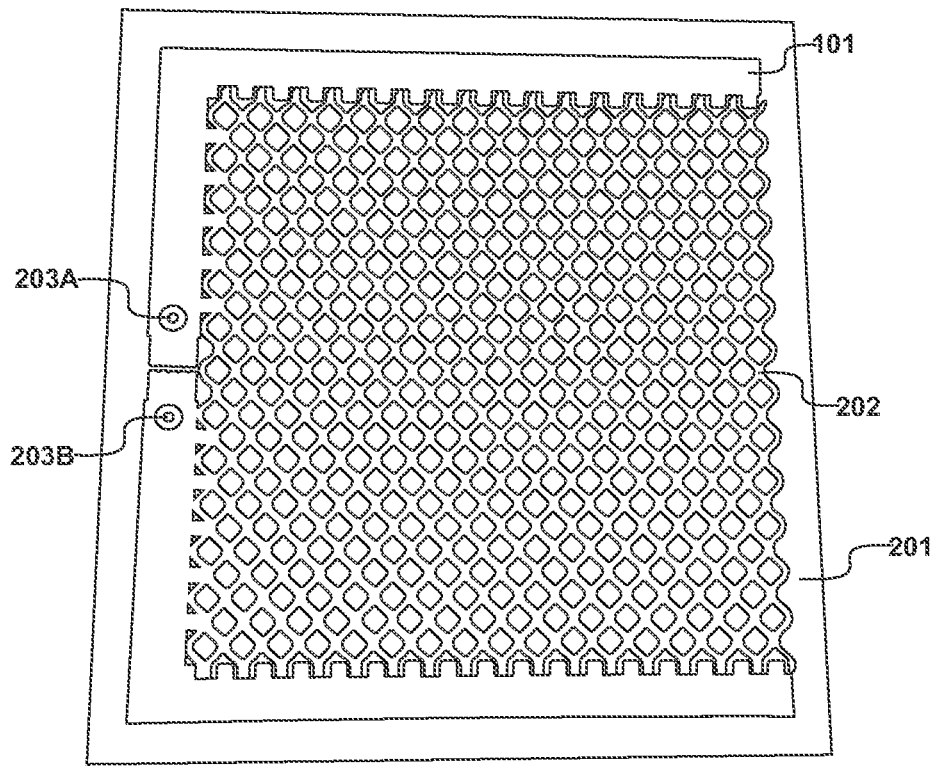
FIG. 2 shows an embodiment of a conductive transfer illustrating a plurality of tessellated cells.

A plan view of conductive transfer 101 falling outside the scope of the claimed invention is illustrated in FIG. 2. In the embodiment, conductive transfer 101 has been applied to a textile 201.

Conductive transfer 101 comprises a plurality of tessellated cells 202 which are defined by conductive layer 104 and a printed conductive ink. In the embodiment, non-conductive layer 102 has also been printed in a form that is substantially similar to the pattern of conductive layer 103. Thus, non-conductive layer 102 is also considered to comprise a plurality of tessellated cells.

In the embodiment, tessellated cells 202 are arranged to form a grid-like pattern. It is appreciated that the tessellated cells may be arranged in any suitable grid-like pattern, and example embodiments herein present possible variations in the tessellated cells rather than an exhaustive list.

Conductive transfer 101 further comprises electrical contacts 203A and 203B. These electrical contacts correspond to the portion 109 previously indicated in FIG. 1 and provide access to conductive layer 104 to allow an electrical current to be supplied to conductive layer 104 to provide functionality to the transfer.

FIG. 3

Figure 3:
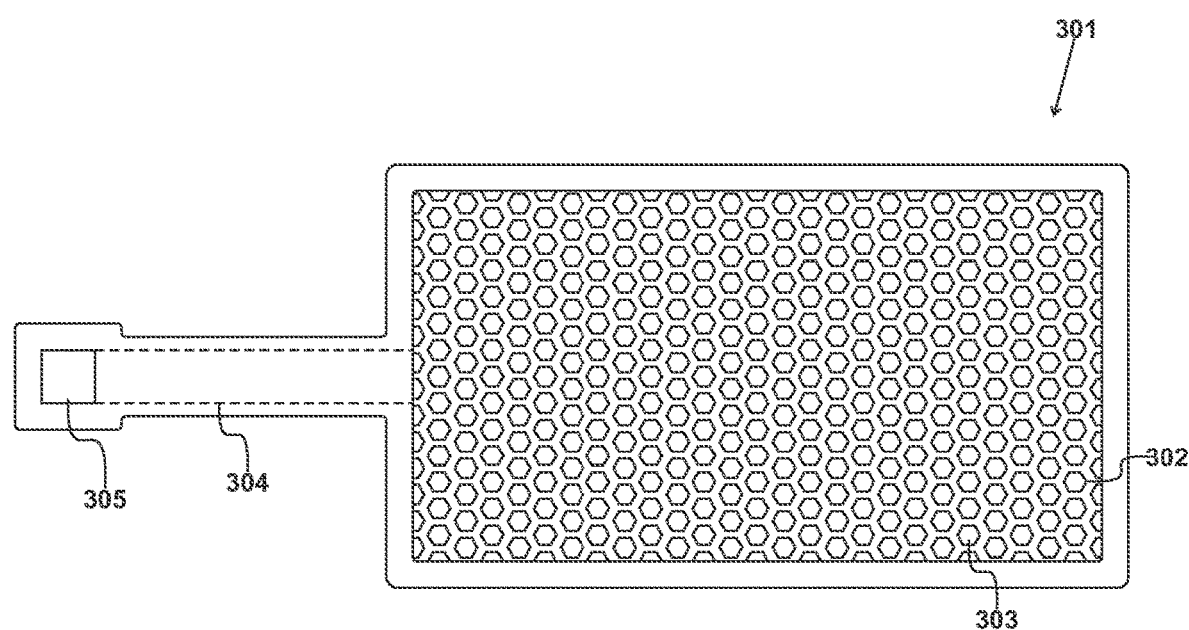
FIG. 3 shows an alternative embodiment of a conductive transfer having a plurality of tessellated cells arranged in the form of a honeycomb pattern.

A further example embodiment of a conductive transfer falling outside the scope of the present invention is shown in FIG. 3 in plan view.

Conductive transfer 301 comprises first and second non-conductive layers in a substantially similar manner to those as illustrated in respect of conductive transfer 101. Between the two non-conductive layers is a conductive layer which comprises a plurality of tessellated cells 302 defined by a printed conductive ink.

In the embodiment, the plurality of tessellated cells are arranged in the form of a honeycomb pattern over a main element 303 of the conductive layer. The conductive layer of transfer 301 comprises main element 303 and an input track 304, which is shown as dashed lines to illustrate where it is partially overprinted by one of the non-conductive layers.

Input track 304 extends towards one end of conductive transfer 301 and presents an exposed electrical contact point 305 which can be used to connect to, for example, a power source to provide an electric current to the conductive layer. In this embodiment, input track 304 is printed in the form of a solid input track of conductive ink which connects to main element 303 which is printed in the form of honeycomb tessellated cells. The upper non-conductive layer is printed on the conductive layer and includes an open portion which allows for the creation of contact point 305. In this illustrated embodiment, first non-conductive layer is printed in a substantially similar honeycomb pattern over the conductive layer. In the embodiment, it is appreciated that second non-conductive layer may be printed with a substantially similar honeycomb pattern. However, in a further embodiment, second non-conductive layer is printed as a solid main element.

The pattern of tessellated cells for the conductive layer provides a number of advantages over a solid conductive layer. As will be appreciated, each of the tessellated cells includes an inner cell which is absent of conductive material. Thus, the outline of the tessellated pattern, in this case the honeycomb pattern, reduces the volume or quantity of ink required to print a given sized conductive transfer. This in turn reduces the weight of the conductive transfer which can be particularly desirable in respect of transfers which are provided for use with wearable items. Furthermore, when transferred to a textile or fabric, the inner cells provide apertures in the conductive layer which improves the flexibility and stretchability of the tessellated area. This allows the transfer to be applied to conventional stretchable textiles without loss of functionality. In addition, a patterned tessellation such as the honeycomb pattern shown in FIG. 3 also provides an even electrical current flow when an electrical current is provided via contact point 305.

Experiments conducted by the applicant have also indicated that functionality is also retained if damage is suffered to some of the tessellated cells. For example, if there is a break in the pattern on one part of the grid, the electrical current is able to redirect via one of the other cells.

Figure 4:
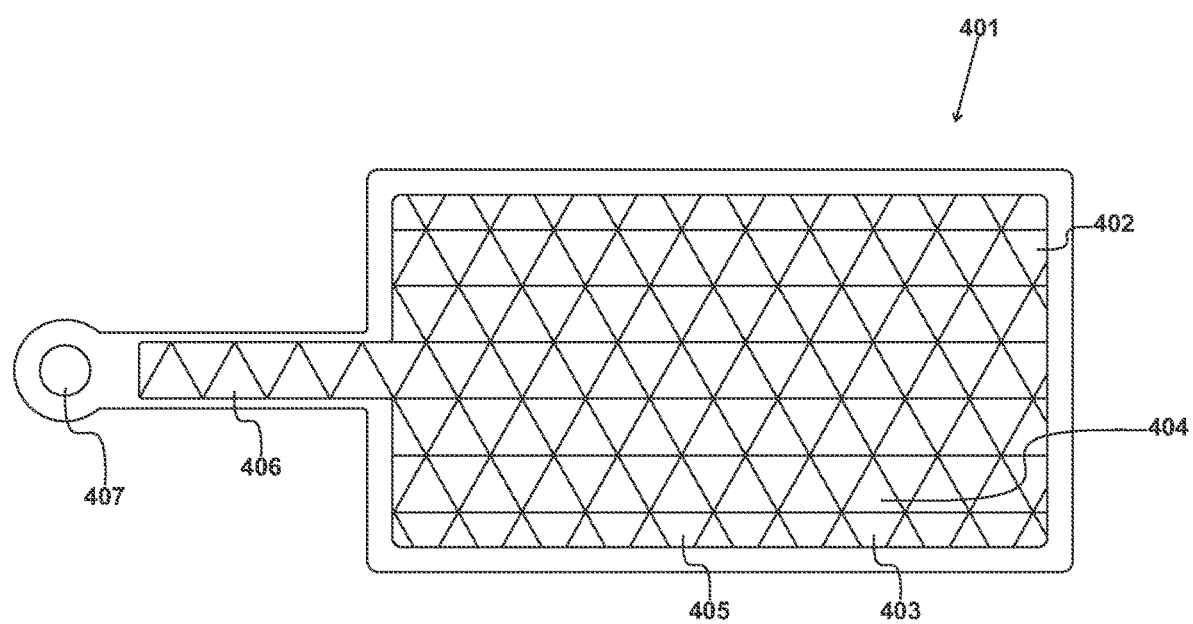
FIG. 4 shows a further alternative embodiment of a conductive transfer having a plurality of tessellated cells arranged in the form of triangular packing.

Consequently, it is appreciated that a similar principle applies when other patterns are utilized, a further example of which is illustrated in respect of FIG. 4.

FIG. 4

An alternative example embodiment of a conductive transfer in accordance with the present invention is shown in FIG. 4 in plan view.

Conductive transfer 401 comprises first and second non-conductive layers and a conductive layer positioned between the two non-conductive layers in a substantially similar manner to conductive transfer 101 as shown in FIG. 1. In the embodiment, conductive transfer 401 comprises a conductive layer which comprises a plurality of tessellated cells 402 defined by a printed conductive ink.

In the embodiment, tessellated cells 402 are arranged to form a grid-like pattern as shown and in the form of triangular packing. Thus, the trace of conductive ink is printed as a series of triangular cells, such as triangular cell 403. In a substantially similar manner to the honeycomb pattern arrangement of FIG. 3, each triangular cell includes an inner cell, for example inner cell 404, in which conductive ink has not been printed.

In the embodiment, conductive transfer 401 comprises a main element 405 and an input track 406. In this particular embodiment, the plurality of tessellated cells 402 are comprised over both main element 405 and input track 406. Consequently, input track 406 can have increased flexibility and stretchability. It is appreciated that, for a particular application, the cross-sectional area of the input track in part determines the amount of electrical current which can flow along the input track. Consequently, in some embodiments, input track 406 may have an increased cross-sectional area to ensure a desired electrical current is achieved.

As with conductive transfer 301, input track 406 extends from main element 405 towards one end whereby the non-conductive layer provides a portion which is utilized as an electrical contact point 407.

It is appreciated that, in this embodiment, the tessellated cells are arranged in a triangular packing pattern. In an alternative embodiment, the tessellated cells are arranged in a circular packing arrangement. It is further appreciated that any other suitable packing arrangement may be utilized for the tessellated cells as desired, however, in each embodiment in accordance with the claimed invention the tessellated cells are such that they comprise a cell with an outline defined by the conductive ink and an inner cell which is substantially absent of conductive ink so as to present an aperture in the conductive layer.

In the embodiment, it is appreciated that the first non-conductive layer of conductive transfer 401 also comprises a substantially similar triangular packing pattern. In alternative embodiments, however, first non-conductive layer of conductive transfer 401 may be printed as a solid input track and main element. In a further embodiment, the non-conductive layer may comprise an alternative patterned effect. In one example, this patterned effect may be simulated to give the appearance of another material, for example, leather. In this way, the conductive transfer may be utilized on the surface of another item or textile such as a car seat, car interior or similar. In one embodiment, the conductive transfer may be used to provide a circuit for a heated seat.

FIG. 5

Figure 5:
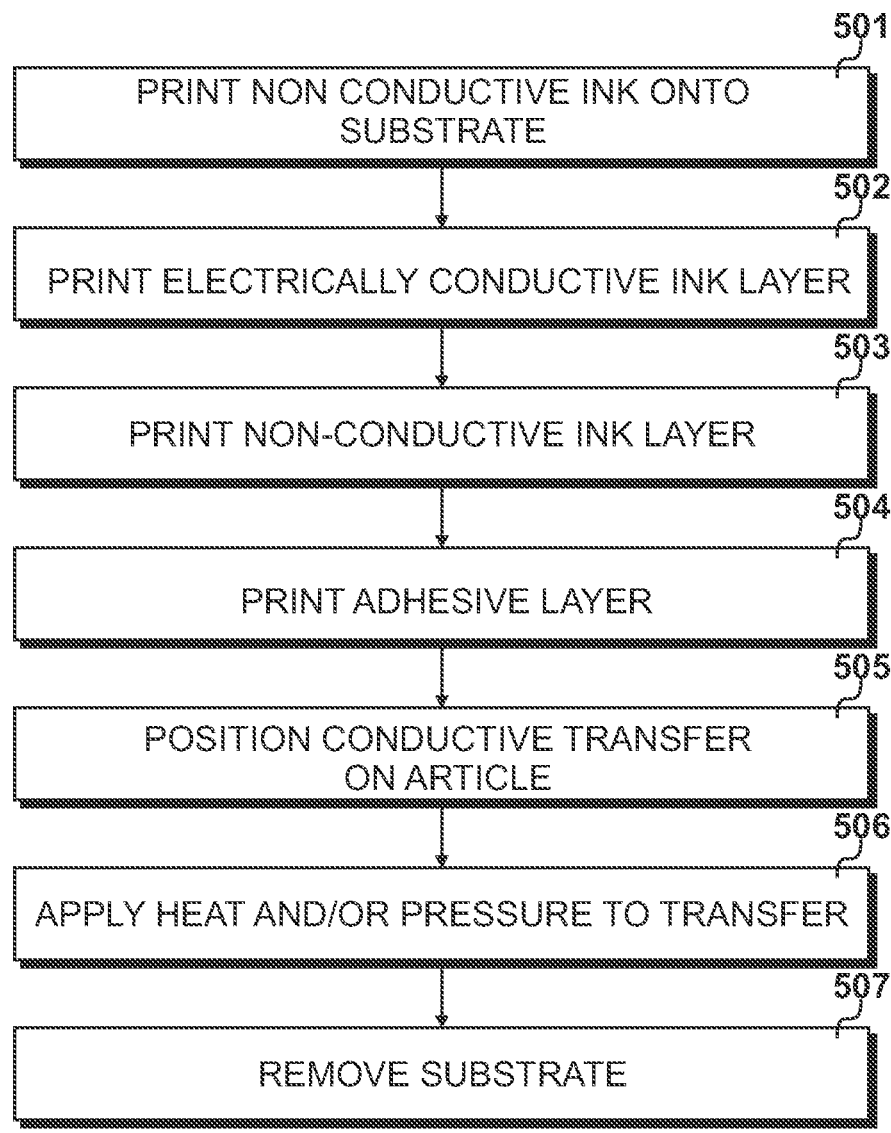
FIG. 5 shows a method of producing a conductive transfer in accordance with the present invention and apply the transfer to an article.

A schematic diagram showing a method of producing any of conductive transfers described herein is shown in FIG. 5. At step 501, a suitable non-conductive ink is printed onto a transfer substrate, such as substrate 106 to produce a first non-conductive layer. Once printed, the first non-conductive layer may be cured as necessary before an electrically conductive ink is printed thereon at step 502. This step thereby produces a conductive layer, which again may undergo any suitable curing process.

At step 502, the electrically conductive ink is printed in a pattern which comprises a plurality of tessellated cells which are defined by the printed conductive ink.

At step 503, substantially similar non-conductive ink is printed over the conductive layer to produce a second non-conductive layer. Again, once printed, the second non-conductive layer may undergo a suitable curing process to ensure it is suitable for application of the adhesive material. At step 504, the adhesive material is printed over the second non-conductive layer to produce the adhesive layer. A further curing step may be included thereafter.

Once the printing process of steps 501 to 504 have been completed, the conductive transfer will be in a similar form to that of FIG. 1 on a transfer substrate 106. Steps 505 to 507 provide a method of attaching the conductive transfer to an article. At step 505, the conductive transfer is positioned onto an article. The adhesive layer is brought into contact with the article such that the transfer substrate 106 is furthest away from the surface of the article.

At step 506, an application of heat, pressure or a combination of both heat and pressure is applied to the transfer such that the adhesive layer allows the transfer to adhere to the article.

Once adhered successfully, transfer substrate 106 can be peeled away and removed leaving the first non-conductive layer as the top surface of the transfer on the article.

FIG. 6

Figure 6:
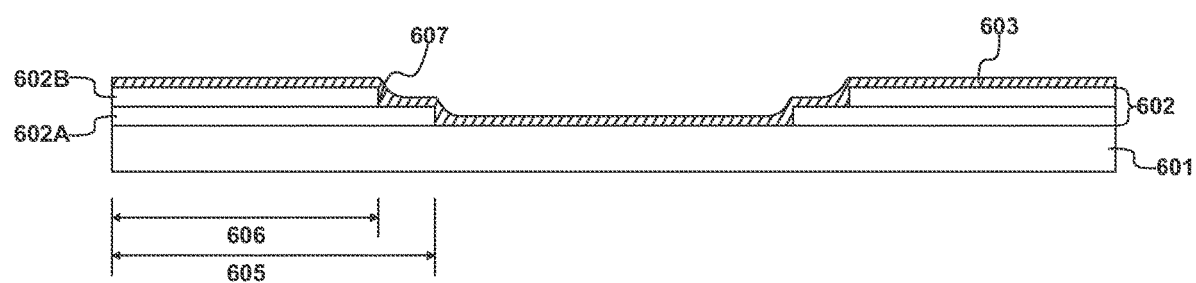
FIG. 6 shows a printed stepped layer of the conductive transfer for improving durability.

In order to ensure increased durability of the conductive transfer in use, the aforementioned printing method may include printing additional layers of material in the manner described in FIG. 6.

In this illustrated example, transfer substrate 601 has, in accordance with step 501 described previously, has a non-conductive layer 602 printed thereon. In this embodiment, non-conductive layer 602 comprises a first printed ink layer 602A and a second printed ink layer 602B which have been printed separately. In this way, a first pass of the printing method is made to produce layer 602A, and a second pass is made to produce layer 602B. Conductive layer 603 is printed over the non-conductive layer in line with step 502.

In the embodiment, conductive layer 603 forms a contact point 604 as illustrated. However, in conventional methods, known non-conductive layers provide a waterfall-effect of the conductive layer over the edge of the non-conductive layer. This can lead to instability in the conductive layer and may lead to breakages. To avoid this problem, in the area of the contact point 604, printed ink layer 602A comprises a first length 605 and printed ink layer 602B comprises a second length 606. Second length 606 is shorter than first length 605 and, a step 607 is formed between the first and second printed ink layers.

Thus, this creates a stepped layer which avoids the waterfall-effect. Consequently, durability and effectiveness of the conductive transfer are improved in this way.

FIG. 7

Figure 7:
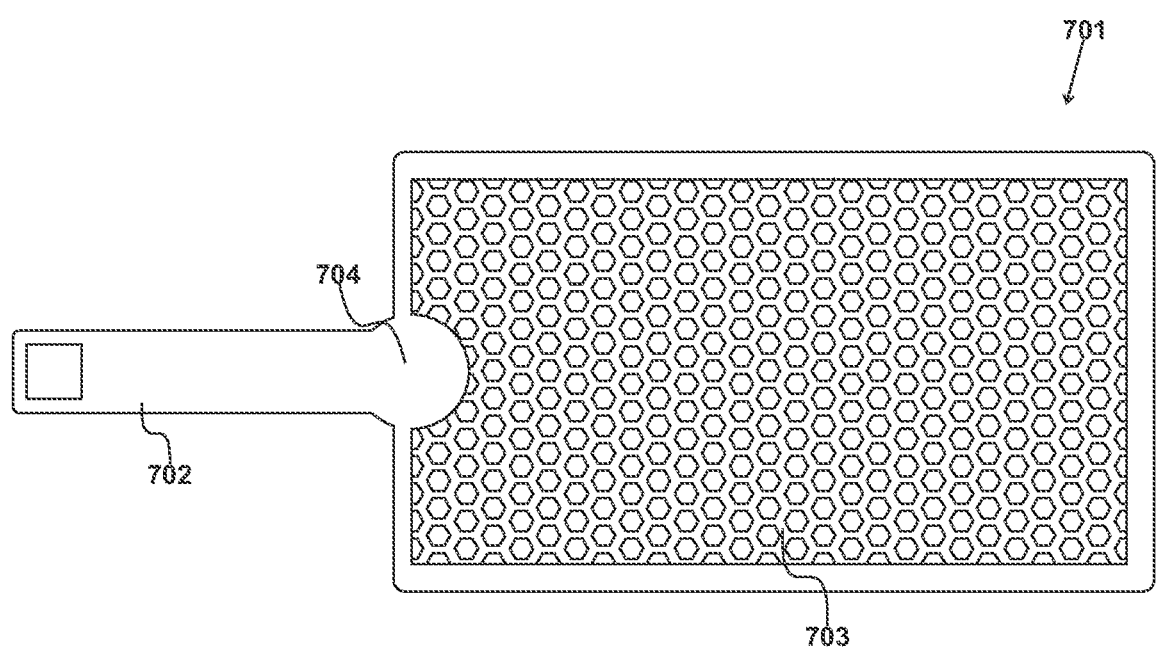
FIG. 7 shows a further embodiment of a conductive transfer.

A further illustration of the increased durability of the conductive transfer described herein is shown in FIG. 7, whereby, in respect of conductive transfer 701, the cross-sectional area of the interface between the input track 702 and main element 703 has been increased. In all other respects, conductive transfer 701 can be considered substantially similar to conductive transfer 301.

At the point of the interface, the conductive transfer has been widened to include a substantially spherical interface 704 which comprises an increased cross-sectional area. In particular, the width of input track 702 is less than the diameter of the spherical interface 704.

This again provides an advantage of increased durability and robustness around the interface, and reduces the stress over the cross-sectional area.

FIG. 8

It is appreciated that any of the conductive transfers described herein may be utilized and attached to any suitable article. Examples include a wearable item, a heated seat, a heated blanket, a heat sensor, a medical bandage, a medical pad or a heated pad. It is appreciated however, that this list should not be considered exhaustive.

Figure 8:
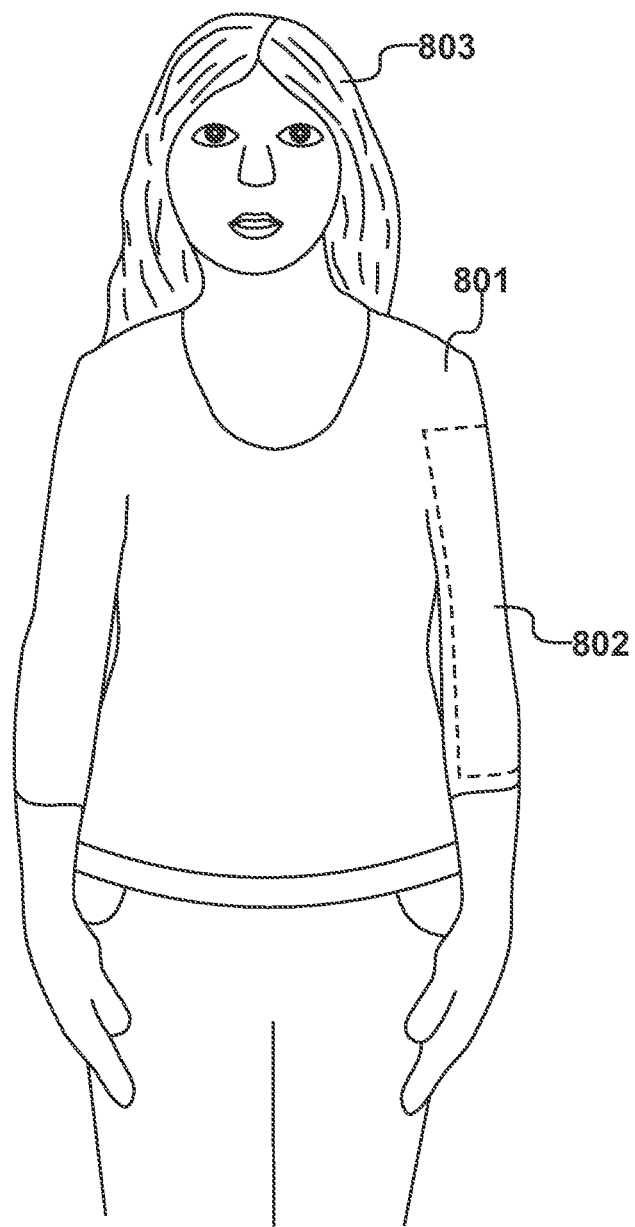
FIG. 8 shows a wearable item incorporating a conductive transfer in accordance with the present invention.

In one example embodiment, any of the aforementioned conductive transfers may be applied to the wearable item of FIG. 8. In the embodiment, a conductive transfer of the type herein described is applied to wearable item 801. Wearable item 801 is a conventional top or shirt and conductive transfer 802 is applied on the inside of a sleeve of the wearable item.

In the embodiment, conductive transfer 802 is configured to provide electrical muscle stimulation (EMS) and is incorporated into wearable item 801 such that is it able to be worn close to the skin of wearer 803 and apply EMS to the wearer.

While conductive transfer 802 in this embodiment is worn close to the skin of the user's arm, it is appreciated that wearable items incorporating conductive transfers for use close to the skin may be provided in any embodiments relating to, but not limited to the following: sexual health, urinary & fecal incontinence, pain relief and management, toning & strengthening of muscles, neuromuscular rehabilitation, orthopedic rehabilitation, muscle control in the avoidance of injuries. In further embodiments, as an alternative to providing electrical muscle stimulation, the conductive transfer is configured to measure vital signs of a wearer of an article to produce an electrocardiogram (ECG). In still further embodiments, other biosensors may be used, such as, but not limited to, Electroencephalogram (EEG), Electromyogram (EMG), Galvanic skin response (GSR) or Magnetoencephalogram (MEG).

Referring back to the embodiment of FIG. 8, conductive transfer 802 is configure to provide EMS to wearer 803, in particular in relation to wearer 803's arm. In a particular embodiment, conductive transfer 802 is configured to have a plurality of activation zones. For example, a first plurality of tessellated cells may correspond to a first activation zone and a second plurality of tessellated cells may correspond to a second activation zone. Thus, wearer 803 can ensure that a specific activation zone can be utilized for muscle stimulation.

This can ensure that the required muscles are stimulated, for example, if there are certain muscles which require treatment.

Providing a conductive transfer with tessellated cells also provides a degree of breathability as the spaces in the cells mean that when applied to a textile or wearable item, air is more easily able to pass through. As conventional conductive transfers typically print transfers for such applications in the form of solid conductive layers, in some embodiments whereby the conductive transfer is incorporated into a wearable item, the solid print can cause the transfer to slide around and lose contact with the muscle area to which stimulation is required. In the present application, the tessellated cells provide an addition grip due to the breaks in the pattern ensuring that the transfer stays in the intended position so that stimulation is retained at the point of interest.

Figure 9A:
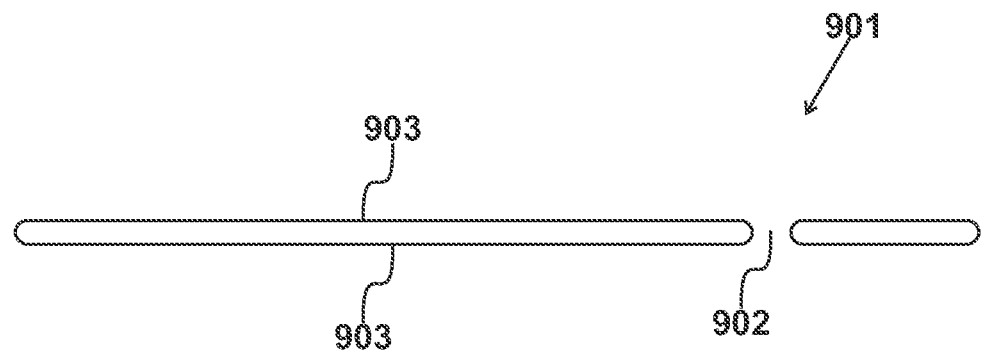
FIGS. 9A and 9B show a method of incorporating a conductive transfer of the type described herein into a textile panel.
Figure 9B:
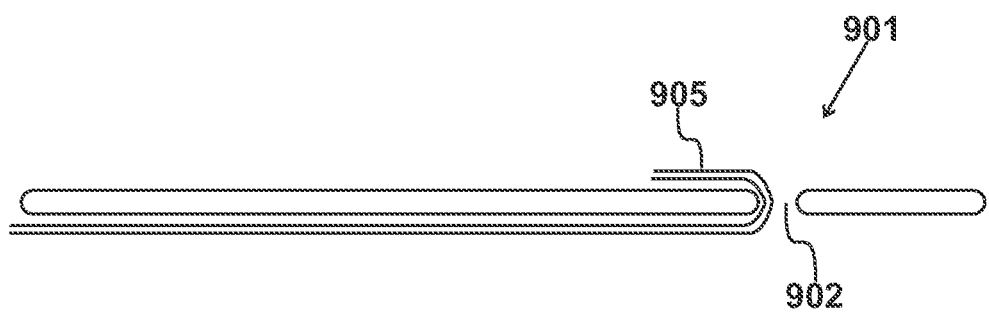

FIGS. 9A and 9B

When incorporating such a conductive transfer as described herein into a wearable item, such as wearable item 801 as previously described, during manufacture there are a number of considerations so as to ensure that the conductive transfer is still able to function as an electrical circuit in accordance with any of the aforementioned applications.

Conventionally, wearable items comprise seams whereby a one or more textile panels can be brought together to result in a wearable item. In FIG. 9A, a textile panel 901 has been provided with an aperture 902 therethrough. Textile panel 901 comprises a first top surface 903 and a second bottom surface 904, which is position substantially opposite to surface 903.

In the embodiment, in FIG. 9B, conductive transfer 905 is affixed to textile panel 901 by positioning conductive transfer 905 through aperture 902 and affixing the conductive transfer 905 to both first surface 903 and second surface 904. This may be achieved by the application of heat and/or pressure previously indicated once the conductive transfer has been positioned through aperture 902.

While it is appreciated that the embodiment of FIG. 9 can be applied to a conductive transfer of the type described herein, it is further appreciated that the process described may also be suitable for other conductive transfers beyond the scope of this application.

Figure 10A:
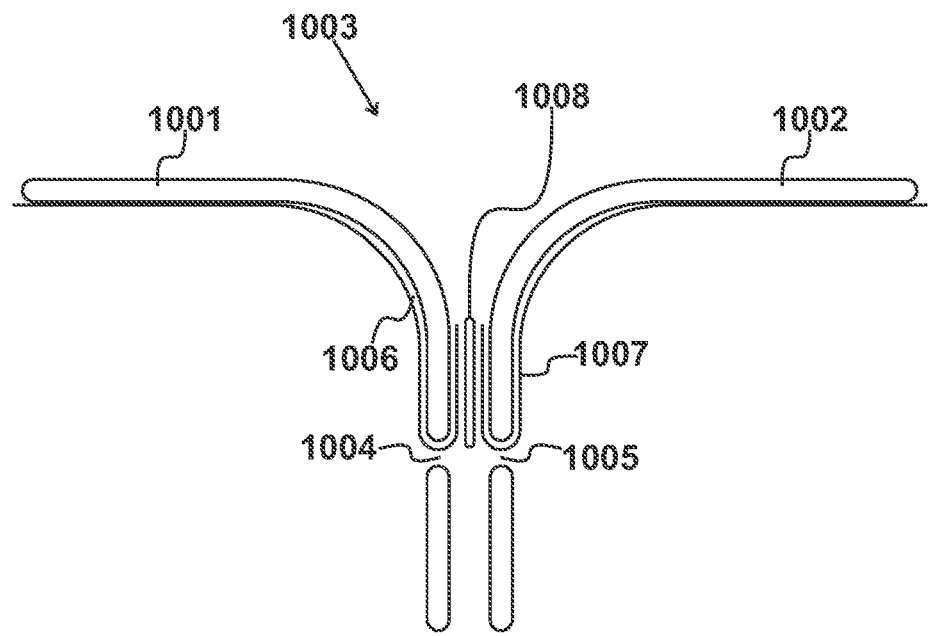
FIGS. 10A and 10B show a seam including a conductive transfer with additional stitching.
Figure 10B:
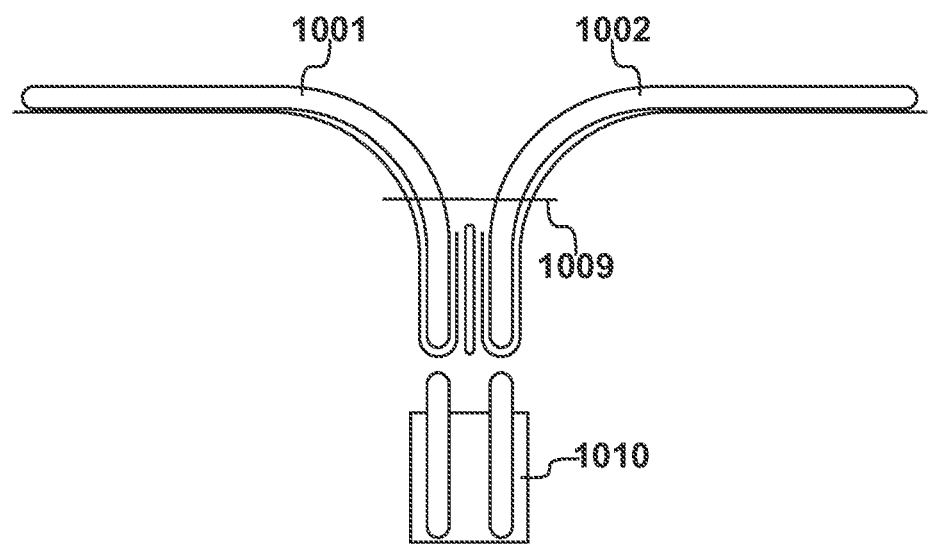

FIGS. 10A and 10B

A particular advantage of the tessellated cells of the present invention means that, when incorporated into a textile which requires stitching, a stitch which penetrates the conductive transfer, whether intended or not, is less likely to have a negative effect on the operational functionality of the transfer. In particular, stitching may be specifically designed to ensure that during manufacture, the stitches in the fabric and potentially across the conductive transfer penetrate through the tessellated cells themselves rather than the conductive trace on the conductive layer. In addition, as will be appreciated, given that it is possible for the conductive transfer to function effectively if a small number of the tessellated cells are damaged, a stitch may penetrate part of the conductive trace without any adverse effects.

In one embodiment, as will now be described, in an article comprising a textile and a conductive transfer as described herein, the textile comprises a seam comprising at least one stitch and the at least one stitch penetrates the textile via a point within a first one of the tessellated cells.

As shown in FIG. 10A, a first textile panel 1001 and a second textile panel 1002 are arranged to form a seam 1003. Each textile panel 1001 and 1002 comprises and aperture 1004 and 1005 respectively through which conductive transfers 1006 and 1007 respectively are positioned therethrough.

In order to bring textile panel 1001 and textile panel 1002 together to form seam 1003, an anisotropic conductive film (ACF) 1008 is positioned between textile panel 1001 and textile panel 1002 thereby providing an electrical connection through ACF bonding. Anisotropic conductive film (ACF) is a known film which is used to bond components together following the application of heat and pressure. It is appreciated that, alternatives to ACF may be utilized in alternative embodiments, for example, conductive adhesives, low temperature solder or cured inks such as silver.

In FIG. 10B, once textile panels 1001 and 1003 have been brought together and bonded, a conventional stitching process can be carried out. A first stitch 1009 is positioned across the seam 1003 and a conventional overlocking stitch 1010, performed by an overlocker sewing machine, is used to hold the textile panels together.

As noted, it is possible to stitch between tessellated cells to avoid damage to the conductive layer of the conductive transfer. In particular, it is possible to provide the overlocker machinist with a guide which ensures that stitches are made at specific intervals which correspond to the sizes of the tessellated cells to ensure that the defined outline is avoided. In this way, the conductive transfer's inclusion into wearable items can be incorporated into existing practices.

Figure 11A:
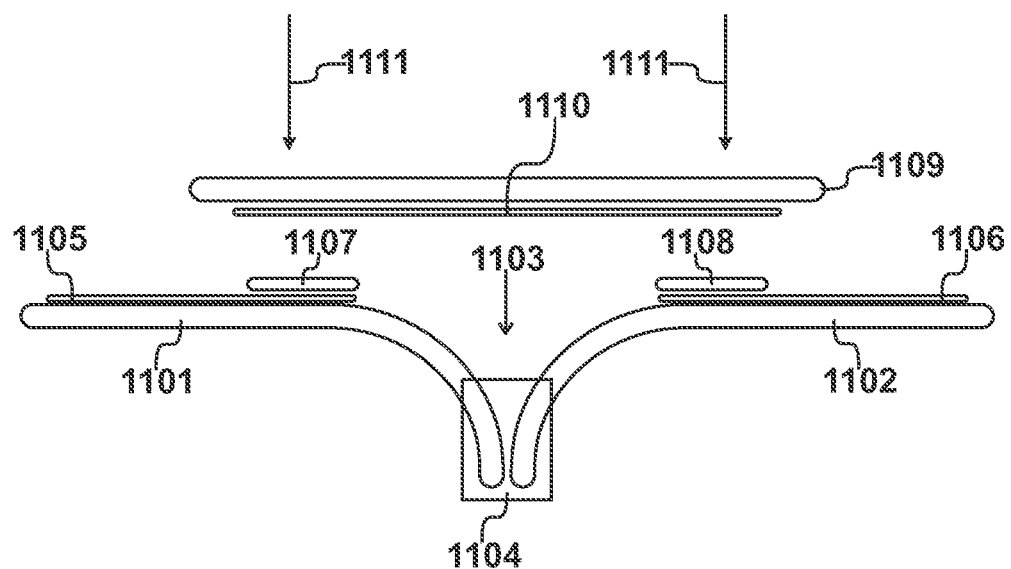
FIGS. 11A and 11B shows the connection of two textile panels and their respective conductive transfers across a seam.
Figure 11B:
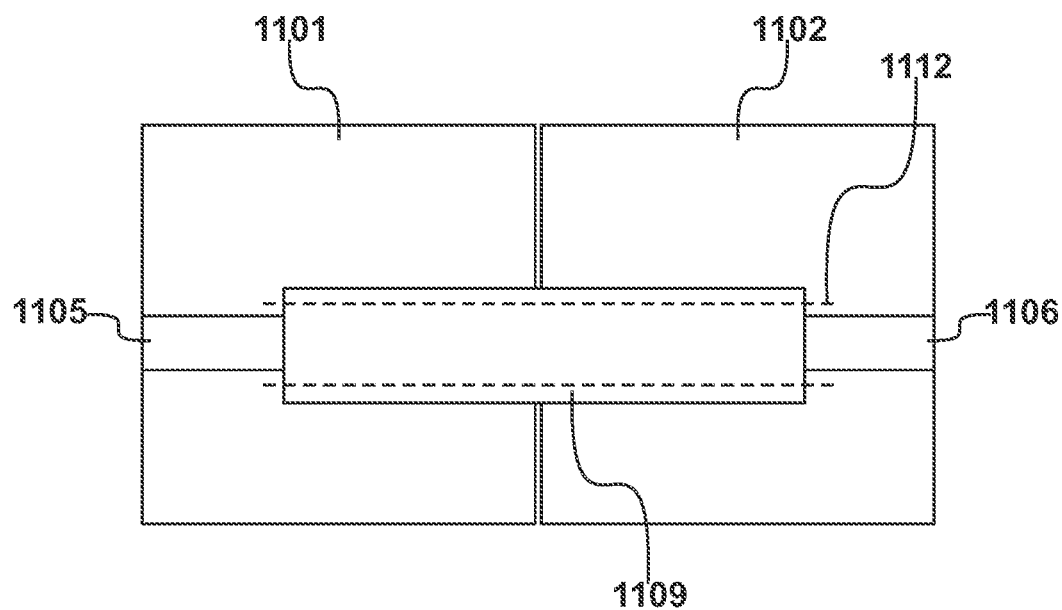

FIGS. 11A and 11B

A further example showing the incorporation of a conductive transfer into an article comprising textile panels is shown in FIGS. 11A and 11B.

FIG. 11A shows textile panel 1101 and textile panel 1102 which form a seam 1103 and which are joined by means of an overlocker stitch 1104. Textile panel 1101 comprises conductive transfer 1105 and textile panel 1102 comprises a conductive transfer 1106. In the embodiment, conductive transfer 1105 and conductive transfer 1106 each include contact points in which it is desirable that those contact points are connected to each other across seam 1103. To achieve this, further anisotropic conductive film (ACF) 1107 and 1108 respectively is positioned over each of the contact points of conductive transfer 1105 and conductive transfer 1106.

To provide the connection, a textile element 1109 which comprises a further conductive transfer 1110 is placed over the conductive transfer 1105 and 1106 and their respective contact points. Conductive transfer 1110 has corresponding contact points which are configured to cooperate with those of conductive transfer 1105 and conductive transfer 1106. Thus, when textile element 1109 is positioned over textile panels 1101 and 1102 as indicated, heat and/or pressure can be applied to textile element 1109 as per arrows 1111 to provide a connection between the conductive transfers across the seam 1103.

FIG. 11B shows a plan view of the arrangement from the top above textile element 1109. With textile panels 1101 and 1102 now joined, additional stitching 1112 can be added to provide extra strengthening across seam 1103.

Figure 12A:
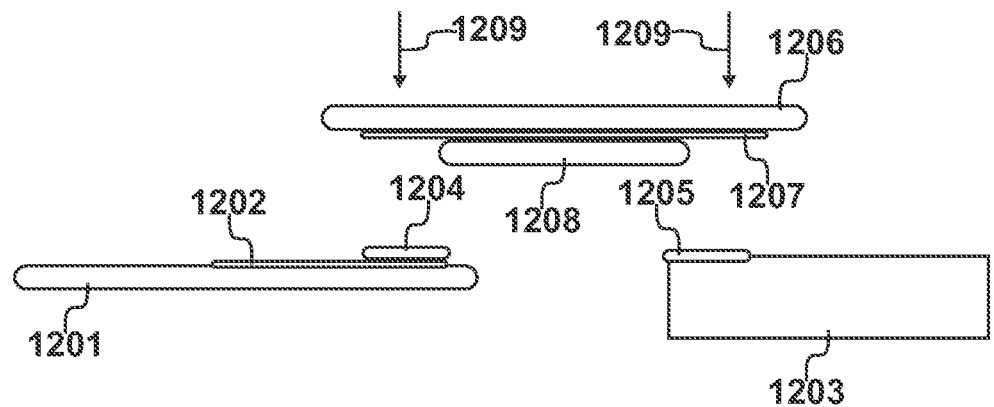
FIGS. 12A and 12B show the connection of a textile panel comprising a conductive transfer to an electronic component.
Figure 12B:
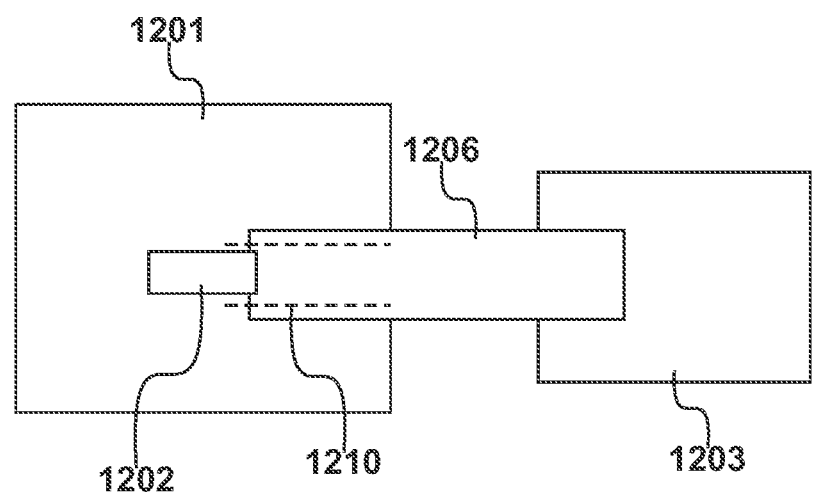

FIGS. 12A and 12B

A conductive transfer of the type described herein can further be connected to an electronic component such as a power source, for example, a battery, a printed circuit board, a connector or any other suitable or required electronic component.

Connection of such a conductive transfer can be achieved in a similar manner to the connection of two conductive transfers across a seam as described in FIGS. 11A and 11B. In FIG. 12A, a textile panel 1201 comprising a conductive transfer 1202 is provided, along with any suitable electronic component 1203, such as those previously described. Conductive transfer 1202 includes a contact point which requires connection to electronic component 1203, which also includes a corresponding contact point for making an electrical connection. To connect the conductive transfer 1201 to electronic component 1203, anisotropic conductive film (ACF) 1204 and 1205, is placed respectively on the contact points of conductive transfer 1201 and electronic component 1203.

A textile element 1206 is provided which comprises a conductive transfer 1207, which again includes two corresponding contact points on its surface. A further textile element 1208 sandwiches conductive transfer 1207 between textile element 1206 and textile element 1208 while retaining exposure to the two contact points of conductive transfer 1207.

On further application of heat and/or pressure to textile element 1206, as indicated by arrows 1209, the contact points of conductive transfer 1207 connect with conductive transfer 1202 and electronic component 1203. Textile element 1208 provides a clean undersurface which also obscures the view of conductive transfer 1207 in use and presents a textile appearance on the undersurface.

FIG. 12B shows a corresponding plan view, whereby conductive transfer 1202 is connected to electronic component 1203. Again, additional stitching 1210 can be provided to strengthen the seams of the textile or wearable item.

FIG. 13

Figure 13:
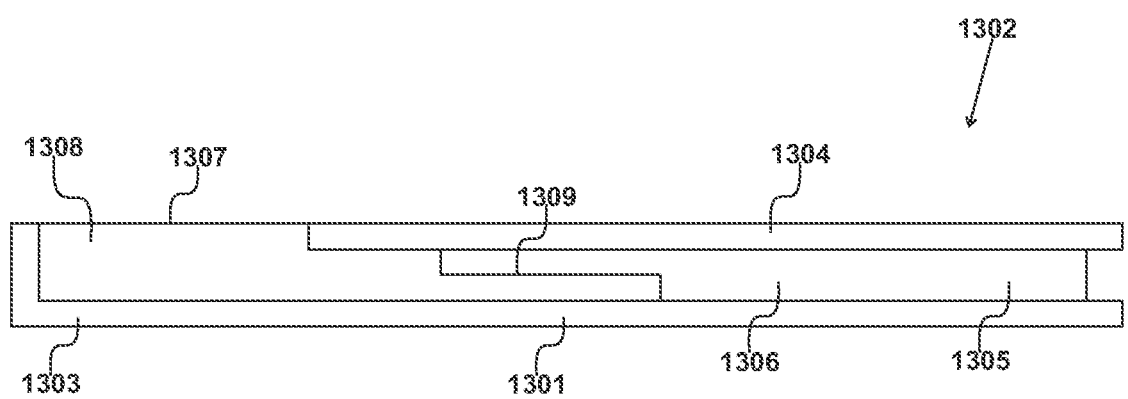
FIG. 13 shows an arrangement of the conductive layer of a conductive transfer to improve washability.

In order to further improve the conductive transfers described herein, the conductive layer of a conductive transfer can be manufactured such that it is more durable to conventional washing practices. FIG. 13 shows a section of input track 1301 of a conductive transfer 1302.

Conductive transfer 1301 comprises non-conductive layer 1303 and non-conductive layer 1302 which are substantially similar to the non-conductive layers described previously. Conductive layer 1304, however, in this illustrated embodiment, comprises two separate materials. A first, highly conductive material 1306 is printed across the conductive layer in the portion which, in the finished conductive transfer 1302, is encapsulated by non-conductive layer 1303 and non-conductive layer 1304. In the portion which comprises contact point 1307, however, a second highly washable material 1308 is printed.

In the embodiment, highly washable material 1308 comprises a conductive polymer which comprises a PEDOT/PSS (3,4 polyethylene dioxythiophene base material. Highly conductive material 1306 comprises a stretchable silver ink. This arrangement keeps the conductive material 1306 away from being exposed to a standard wash, for example of a wearable item in a washing machine. Between the highly conductive material 1306 and the highly washable material 1308 is a contact zone 1309 which ensures a good connection between the two materials.

The invention claimed is:

1. A conductive transfer (101, 201, 301, 401, 701, 802, 905, 1006, 1007) for application to an article (801), comprising:
   a first non-conductive layer (102, 602) and a second non-conductive layer (103);
   a conductive layer (104, 603) positioned between said first non-conductive layer and said second non-conductive layer; and
   an adhesive layer (105) for adhering said conductive transfer to an article; wherein
   said conductive layer comprises a plurality of tessellated cells (302, 402) defined by a printed conductive ink, said tessellated cells are arranged to form a grid-like pattern wherein each of the tessellated cells includes an inner cell (404) which is absent of conductive material, and characterised in that:
   said conductive layer comprises a main element (303, 405, 703) and an input track (304, 406, 702) and said plurality of tessellated cells are comprised over said input track of said conductive layer;
   said first non-conductive layer comprises a first printed ink layer (602A) and a second printed ink layer (602B), said first printed ink layer comprising a first length (605); and
   said second printed ink layer comprises a second length (606) shorter than said first length, and said second printed ink layer overlays said first printed ink layer to form a step (607) between the first and second printed ink layers.

2. A conductive transfer according to claim 1, wherein said tessellated cells are arranged in the form of a honeycomb pattern.

3. A conductive transfer according to claim 1, wherein said tessellated cells are arranged in the form of circular packing or triangular packing (403).

4. A conductive transfer according to claim 1, wherein said plurality of tessellated cells are comprised over said main element of said conductive layer.

5. A conductive transfer according to claim 1, wherein said input track comprises an ink comprising a conductive polymer.

6. A conductive transfer according to claim 1, wherein said first non-conductive layer is printed onto a substrate (106, 601).

7. A conductive transfer according to claim 6, wherein said substrate is removable from said first non-conductive layer following an application of heat.

8. A conductive transfer according to claim 6, wherein said substrate is removable from said first non-conductive layer following an application of pressure.

9. A conductive transfer according to claim 1, wherein at least one of said first non-conductive layer or said second non-conductive layer comprises a patterned effect.

10. An article (801) comprising a textile and further comprising said conductive transfer according to claim 1.

11. An article according to claim 10, wherein said textile comprises a seam (1003) comprising at least one stitch (1009) and said at least one stitch penetrates said textile via a point within a first one of said tessellated cells.

12. An article according to claim 10, wherein said conductive transfer is configured to provide electrical muscle stimulation to a wearer (803) of said article.

13. An article according to claim 10, wherein said conductive transfer is configured to measure vital signs of a wearer of said article to produce an electrocardiogram.

14. An article according to claim 10, wherein said article comprises a textile panel (901, 1001, 1002) having an aperture (902, 1004, 1005) therethrough, a first surface (903) and a second surface (904) opposite to said first surface; and
said conductive transfer is positioned through said aperture and affixed to both said first surface and said second surface.

15. An article according to claim 10, wherein said article comprises a first textile panel (1001) having a first aperture (1004) therethrough and a first conductive transfer (1006) positioned through said first aperture; and
a second textile panel (1002) having a second aperture (1005) therethrough and a second conductive transfer (1007) positioned through said second aperture; wherein
said first textile panel and said second textile panel are aligned such that said first conductive transfer and said second conductive transfer are connected to form a seam (1003) between said first and second textile panels.

16. An article according to claim 10, wherein said article comprises a first textile panel (1101) comprising a first conductive transfer (1105) and a second textile panel (1102) comprising a second conductive transfer (1106);
said article further comprising a textile element (1109) comprising a third conductive transfer (1110); wherein
said third conductive transfer electrically connects said first conductive transfer and said second conductive transfer across a seam (1103).

17. An article according to claim 10, wherein said article comprises a first textile panel (1201) comprising a first conductive transfer (1202) and a textile element (1206) comprising a second conductive transfer (1207);
said article further comprising an electronic component (1203); wherein
said second conductive transfer electrically connects said first conductive transfer and said electronic component.

18. An article according to claim 10, wherein said article comprises any one of the following:
a wearable item; a heated seat; a heated blanket; a heat sensor; a medical bandage; a medical pad; a heated pad.

19. A method of producing a conductive transfer (101, 201, 301, 401, 701, 802, 905, 1006, 1007) for application to an article (801), comprising the steps of:
printing a non-conductive ink onto a substrate (106, 601) to produce a first non-conductive layer (102, 602);
printing an electrically conductive ink onto said first non-conductive ink layer to produce a conductive layer (104, 603) comprising a main element (303, 405, 703) and an input track (304, 406, 702);
printing said non-conductive ink over said conductive layer to produce a second non-conductive layer (103); and
printing an adhesive material over said second non-conductive layer to produce an adhesive layer (105); wherein
said step of printing an electrically conductive ink comprises printing said electrically conductive ink in a pattern comprising a plurality of tessellated cells (302, 402) defined by a printed conductive ink where said plurality of tessellated cells are comprised over said input track of said conductive layer, wherein said tessellated cells are arranged to form a grid-like pattern wherein each of the tessellated cells includes an inner cell (404) which is absent of conductive material, and characterised in that:
said step of printing said first non-conductive layer comprises printing a first printed ink layer (602A) and a second printed ink layer (602B), and
said first printed ink layer comprises a first length (605), and said second printed ink layer comprises a second length (606) shorter than said first length, and said second printed ink layer printed to overlay said first printed ink layer to form a step (607) between the first and second printed ink layers.

20. A method of producing a conductive transfer for application to an article according to claim 19, further comprising the step of:
attaching said conductive transfer to an article by applying at least one of heat or pressure to said adhesive layer.

21. A method of producing a conductive transfer for application to an article according to claim 20, wherein said step of attaching comprises the steps of:
positioning said conductive transfer through an aperture of said article; and
affixing said conductive transfer to a first surface of said article and a second surface of said article, said second surface being positioned opposite said first surface.

22. A method of producing a conductive transfer for application to an article according to claim 20, wherein said article comprises a textile and said textile comprises a seam, said method further comprising the step of:
stitching across said seam such that at least one stitch penetrates said textile via a point within a first one of said tessellated cells.

* * * * *